United States Patent [19]

Chadwick et al.

[11] Patent Number: 4,888,435
[45] Date of Patent: Dec. 19, 1989

[54] INTEGRATED PROCESS FOR ALKYLATION AND REDISTRIBUTION OF HALOSILANES

[75] Inventors: Kirk M. Chadwick, Hanover; Roland L. Halm, Madison, both of Ind.; Brian R. Keyes, Salt Lake City, Utah

[73] Assignee: Dow Corning Corporation, Midland, Mich.

[21] Appl. No.: 370,209

[22] Filed: Jun. 22, 1989

[51] Int. Cl.$^4$ .............................. C07F 7/08; C07F 7/12
[52] U.S. Cl. .................................................... 556/469
[58] Field of Search .......................................... 556/469

[56] References Cited

U.S. PATENT DOCUMENTS

| | | | |
|---|---|---|---|
| 2,403,370 | 7/1946 | Hurd | 260/607 |
| 2,647,136 | 7/1953 | Sauer | 556/469 |
| 2,647,912 | 8/1953 | Barry et al. | 556/469 |
| 2,717,257 | 9/1955 | Bluestein | 556/469 |
| 3,135,778 | 6/1964 | Sleddon | 260/448.2 |
| 3,655,710 | 4/1972 | Bazouin et al. | 556/469 |
| 4,155,927 | 5/1979 | Straussberger et al. | 260/448.2 E |
| 4,552,973 | 11/1985 | Feldner et al. | 556/469 |
| 4,599,441 | 7/1986 | Kanner et al. | 556/469 |

FOREIGN PATENT DOCUMENTS 1162478A 6/1985 U.S.S.R. .............................. 556/469

OTHER PUBLICATIONS

Hurd, J. Am. Chem. Soc., (1945), vol. 67, pp. 1545–1548.

Primary Examiner—Paul F. Shaver
Attorney, Agent, or Firm—James E. Bittell

[57] ABSTRACT

An improved process for the preparation of multi-organic substituted silanes from the reaction of halides of silicon with an alkyl halide in the presence of a halogen-accepting metal is described. The improvement integrates a redistribution process into the alkylation process. The redistribution process involves an interaction between a multi-organic substituted silane and a halosilane with fewer organic substituents whereby an organic group from the multi-organic substituted silane is exchanged with a halogen group of the less organic substituted halosilane.

28 Claims, No Drawings

INTEGRATED PROCESS FOR ALKYLATION AND REDISTRIBUTION OF HALOSILANES

BACKGROUND OF THE INVENTION

This invention relates to the redistribution of organic substituents of halides of silicon to produce more multi-organic substituted silanes. More specifically, this invention relates to a process in which an alkylation step is coupled with a redistribution step to facilitate conversion of halosilanes and organohalosilanes, for example $SiCl_4$ and $CH_3SiCl_3$, to more economically valuable multi-organic substituted species such as $(CH_3)_2SiCl_2$, $(CH_3)_3SiCl$ and $(CH_3)_4Si$.

In the silicones industry the multi-organic substituted species such as $(CH_3)_2SiCl_2$ and $(CH_3)_3SiCl$ are often in high demand and short supply. Diorganodihalosilanes are hydrolyzed to produce diorganopolysiloxane polymers. These polymers find numerous applications as fluids and formulation components of silicone gels, elastomers and resins. Triorganohalosilanes are in demand as end-blockers and as silylating agents.

Organohalosilanes are produced primarily by a process of reacting silicon directly with organic halides, as first disclosed by Rochow and his co-workers in the 1940's. This direct process can be controlled so that the predominant component is the diorganodihalosilane. However, other products of lesser commercial utility are also produced. These other products include tetrahalosilanes and organotrihalosilanes. It would be advantageous if such highly halogenated species could be selectively and efficiently converted to the more useful diorganodihalosilanes, triorganohalosilanes, and tetraorganosilanes.

Methylation of an organohalosilane such as methyltrichlorosilane can be facilitated by a halide-accepting metal such as aluminum. This process is believed to encompass the following steps:

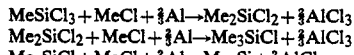
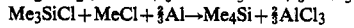

Reaction 1 is considerably slower than reactions 2 and 3 and limits the rate of conversion of methyltrichlorosilane to multi-organic substituted silanes.

Methyltrichlorosilane can also undergo a redistribution reaction as illustrated in reaction 4.

Reaction 4 can be catalyzed by a metal halide such as $AlCl_3$ to increase the redistribution rate.

Hurd, *J. Am. Chem. Soc.* (1945), Vol. 67, p. 1545-1548, and Hurd, U.S. 2,403,370, issued July 2, 1946, disclose the alkylation of tetrachlorosilane and various methylchlorosilanes by passing the vapors of these chlorosilanes together with an alkyl halide over finely divided aluminum, zinc, or other reactive metal at elevated temperature, 300° C. to 500° C. Hurd discloses that a reaction occurs under these conditions in which chlorine groups on the chlorosilane are replaced by alkyl groups.

Sleddon, U.S. 3,135,778, issued June 2, 1964, describes a process using aluminum chloride in the presence of a silane cotaining silicon-bonded hydrogen atoms to redistribute a mixture of trimethylchlorosilane and methyltrichlorosilane to dimethyldichlorosilane.

Turetskaya et al., S.U. 1,162,478 A, June 23, 1985, describes a catalyst powder for methylating chlorosilanes. The catalyst powder consisted of aluminum with 0.05-5 weight percent titanium and up to 100 weight percent silicon powder.

Straussberger et al., U.S. 4,155,927, issued May 22, 1979, discloses a process for preparing trimethylchlorosilane which comprises reacting methyldichlorosilane with methyl chloride and metallic aluminum in the presence of a diatomite.

Halm et. al., Co-pending U.S. patent application Ser. No. 07/258,950, filed Oct. 17, 1988, describes a process for preparing multi-alkylated silanes. The process comprises contacting a halide of silicon, with an alkyl halide in the presence of a halogen accepting metal. The process further comprises a catalyst, such as tin, which improves the efficiency of exchange of alkyl groups from the alkyl halide to the halide of silicon.

SUMMARY OF INVENTION

The present invention relates to an improved process for the preparation of multi-organic substituted silanes from the reaction of halides of silicon with an alkyl halide in the presence of a halogen-accepting metal. The improvement integrates a redistribution process into the alkylation process. The redistribution process involves an interaction between a multi-organic substituted silane and a halosilane with less organic substituents whereby an organic substituent from the multi-organic substituted silane is exchanged with a halogen group of the less organic substituted halosilane as illustrated by the equation:

The redistribution process is catalyzed by metal halides, such as $AlCl_3$, which are typically adsorbed on a solid support material and thereby retained in the reaction zone.

The retained metal halides are particularly effective in catalyzing the redistribution of halosilane species such as $SiCl_4$ and $CH_3SiCl_3$, which species are relatively non-reactive or slow reacting in the alkylation process. The species formed by redistribution, such as $(CH_3)_2SiCl_2$, are more reactive in the alkylation process than the initial halosilane and organohalosilane and are more readily converted to still higher organic substituted species. The integrated process also results in a product distribution based on redistribution equilibrium rather than alkylation equilibrium. These characteristics of the integrated process result in faster and more complete conversion of halosilanes to more economically desirable multi-organic substituted species.

DESCRIPTION OF THE INVENTION

The instant invention relates to a process for increasing the number of organic groups on silanes under conditions that will be delineated in the following description. The invention is an improved process for preparing multi-organic substituted silanes having the formula,

where each R is independently selected from a group consisting of methyl, ethyl, and n-propyl; each $R^i$ is independently selected from a group consisting of alkyl, substituted alkyl, alkenyl, aryl, and alkaryl groups; a has a value of 1, 2, 3, or 4, b has a value of 0, 1, 2, or 3 and the sum of a+b is 2, 3, or 4; and X is a halogen atom.

The process comprising:

(A) contacting a halide of silicon, having the formula, $$R^i_b SiX_{(4-b)},$$

where $R^i$, b, and X are defined above;
with an alkyl halide, having the formula, $$RX$$

where R and X are defined above,
in the presence of a metal which serves as a halogen acceptor;

(B) reacting the halide of silicon with the alkyl halide in the presence of the metal at a temperature greater than 200° C. to form an initial reaction mixture; and (C) contacting the initial reaction mixture with a redistribution catalyst;

(D) isolating and separating a multi-organic substituted silane.

In the instant invention, the multi-organic substituted silanes can be, for example, tetramethylsilane, tetraethylsilane, dimethyldiethylsilane, trimethylchlorosilane, dimethyldichlorosilane, triethylfluorosilane, diethyldibromosilane, ethyldimethylchlorosilane, ethylmethyldichlorosilane, propylmethyldichlorosilane, dimethylvinylchlorosilane, triethylallylsilane, methylphenyldichlorosilane, and diphenylmethylchlorosilane.

The halides of silicon which may be enriched in organic groups are selected from halosilanes and organohalosilanes. These materials are represented by the formula, $$R^i_b SiX_{(4-b)},$$

where b and X are defined above. Each $R^i$ can be an alkyl group, for example, a hydrocarbon group containing 1 to 10 carbon atoms; a substituted alkyl group, for example, chloromethyl or trifluoropropyl; an alkenyl group, for example, vinyl, allyl, or hexenyl; or an aryl or alkaryl group, for example phenyl, tolyl, or benzyl.

The halide of silicon can be a halosilane or an organohalosilane. The halosilane can be, for example, tetrachlorosilane, tetrafluorosilane, and tetrabromosilane. The organohalosilane can be, for example, methyltribromosilane, methyltrichlorosilane, methyltrifluorosilane, ethyltribromosilane, ethyltrichlorosilane, ethyltrifluorosilane, n-propyltrichlorosilane, n- butyltrichlorosilane, vinyltrichlorosilane, methylvinyldibromosilane, allyltribromosilane, phenyltrichlorosilane, or phenylmethyldichlorosilane.

The preferred halosilane for this reaction is tetrachlorosilane. The preferred organohalosilanes are the methyl-, dimethyl-, and trimethyl- substituted chlorosilanes and the ethyl-, diethyl-, and triethyl-substituted chlorosilanes. Mixtures of the halosilanes and organohalosilanes either separately or in combination may be alkylated and redistributed by the process of the instant invention.

The alkyl halide of the instant invention can be, for example, methyl bromide, methyl chloride, methyl fluoride, ethyl bromide, ethyl chloride, ethyl fluoride, or n-propyl bromide. Methyl chloride and ethyl chloride are preferred alkyl halides.

The molar ratio of the alkyl halide (RX) and the halide of silicon (Si) fed to the reactor is not critical. The molar ratio can vary depending upon the starting reactants, the desired product, and the reaction conditions. In general, any RX:Si ratio greater than 1.0 is useful but there is no significant advantage to going beyond a ratio of about 5.

Contacting the halide of silicon and the alkyl halide in the presence of a metal which serves as a halogen acceptor, can be effected by known means for gas-solid contact. Such contact can be effected by vaporizing the halide of silicon and the alkyl halide and feeding these vapors combined or separately to a vessel containing the solid metal. The solids can be configured in such contact arrangements as a packed bed, a stirred bed, a vibrating bed, or a fluidized bed.

The metal which serves as a halogen acceptor can be selected from a group consisting of aluminum and zinc. The preferred metal is aluminum. The metal can be in the physical form, for example, of powder, wire, flakes, granules, and chunks. It is preferred that the form of the metal expose as much surface area as possible to facilitate contact with the halide of silicon and the alkyl halide.

In a preferred embodiment of the instant invention a catalyst effective in improving exchange of X atoms of the alkyl halide and halide of silicon with the metal which serves as a halogen acceptor is used. The catalyst can include for example, tin metal and tin compounds, antimony and antimony compounds, copper and copper compounds, aluminum bromide, boron, phosphorous and phosphorous compounds, palladium, iodine, iron chloride, hydrogen halides, mercury and mercury compounds, and mixtures thereof. In considering aluminum as the halogen-accepting metal, the catalyst can further include zinc and zinc compounds, and mixtures thereof alone or in combination with the aforementioned catalysts. It is understood that the catalyst is not limited to these materials or compounds used as examples. Any material or compound which functions to improve contact of the vapors of the reactant alkyl halide and halide of silicon with the halogen-accepting metal is intended to be encompassed by the instant invention. The preferred catalysts are tin and tin compounds. The most preferred catalyst is tin metal.

The optimal level of alkylation catalyst will vary with the particular catalyst. However, most catalysts are effective at concentrations of greater than about 3000 parts per million (ppm) by weight, based upon the weight of the halogen accepting metal. The catalyst can be in the physical form of, for example, powder, granules, flakes, chips, or pellets. The catalyst is mixed with the halogen accepting metal. Alternatively, the catalyst may be alloyed with the halogen-accepting metal.

Products of the alkylation reaction, including unreacted halides of silicon, are further contacted with a redistribution catalyst. The redistribution catalyst is chosen from a group comprising Lewis acids, which are capable of facilitating the transfer of an organic group from a multi-organic substituted silane to a halosilane with less organic substituents.

The redistribution catalyst may be formed in situ or may be formed separate from the reaction and subsequently added. The alkylation reaction and the redistribution reaction may occur concurrently. The concentration and composition of the initial halosilane and organohalosilane feedstocks will determine the relative importance of the alkylation and redistribution reactions in determining the final product. In a preferred embodiment of the present invention, the redistribution catalyst consists essentially of a metal halide. In a more preferred embodiment of the present invention, the redistribution catalyst consists essentially of a metal halide retained by a solid support material. Examples of useful halogen-accepting metals which form metal halides that can serve as redistribution catalyst of the present invention are aluminum and zinc. Preferred are aluminum chloride and zinc chloride. The more preferred redistribution catalyst is aluminum chloride.

The solid support material may be any material which is stable at the reaction temperature and to which the redistribution catalyst will attach. As long as the support material retains an adequate amount of redistribution catalyst to maintain the desired catalytic activity, the method of attachment of the redistribution catalyst to the support material is not important. The redistribution catalyst may be attached to the support material separate from the reaction and then added to the reaction. Alternatively, the redistribution catalyst may be generated during the reaction and be retained by the solid support material in situ. The solid support material may be mixed with the metal or may be separate and down-stream from the metal. The solid support material may be, for example, fumed, precipitated, or ground silica; silica gel, activated carbon, aluminum oxide, ion-exchange resin, titanium metal, titanium oxide, clay, kaolin clay; and plastic and resin powders, particles, and membranes. The preferred solid support materials for this invention are fumed silica, precipitated silica, activated carbon and aluminum oxide.

The concentration of the solid support material required in the reaction will depend upon the solid support material and the redistribution catalyst used. When the redistribution catalyst is retained by the solid support material in situ a useful range of concentration of support material has been found to be about 5 to 95 weight percent of the combined weight of the support material and the metal. A concentration of about 8 to 50 weight percent of the combined weight of the support material and the metal is preferred when the support material is fumed silica, the metal is aluminum, and the halogen is chlorine.

The temperature in the contact zone(s) where alkylation and redistribution occur should be greater than about 200° C. Preferably the temperature in the contact zone(s) should be in a range from about 200° C. to 450° C. More preferably, the temperature should be in a range of about 250° C. to 350° C. Little reaction is projected to take place at temperatures less than 200° C. Temperatures in excess of 350° C. are not desirable since the rate of cleavage of organic groups from silicon can be significant at these higher temperatures. Additionally, the rate of decomposition of alkyl halides at higher temperatures is also increased.

For redistribution, the residence time of the gaseous halides of silicon in contact with the redistribution catalyst should be greater than about 0.5 seconds.

Isolating and separating the multi-organic substituted silanes can comprise:

(E) Separating the metal halide from gaseous multi-organic substituted silanes, unreacted halide of silicon, and unreacted alkyl halide; and (F) isolating the multi-organic substituted silanes from the unreacted halide of silicon and the alkyl halide.

The metal halide can be a vapor under the conditions of the reaction. Separating the metal halide from the multi-organic substituted silanes and remaining reactants can be effected by such known methods as cooling the vapor stream exiting the reaction vessel to a temperature low enough to allow recovery of the metal halide as a solid or liquid while passing the product silanes and remaining reactants through as a vapor. The metal halides can also remain in the reactor. The vapor stream of gaseous product silanes and remaining reactants can be condensed to a liquid crude product. The multi-organic substituted silanes can be isolated in high purity from the remaining reactants by such known methods as distillation.

In another embodiment of the instant invention, the inventors believe the process as described, supra, can be used to prepare mono-alkylated halosilanes when the process is conducted in the presence of sufficient tetrahalosilane. By sufficient is meant the tetrahalosilane is present at a molar ratio greater than 0.4, in relation to the monoalkylated halosilane. Preferred conditions for this embodiment are where the halosilane is tetrachlorosilane; the alkyl halide is methylchloride or ethylchloride; and the metal which serves as a halogen acceptor is aluminum or zinc.

So that those skilled in the art may better understand and appreciate the instant invention, the following examples are presented. These examples are presented to be illustrative and are not construed as limiting the claims as delineated herein.

EXAMPLE 1:

(Not within the scope of the instant invention)

Baseline methylation performance was established for the reaction of $MeSiCl_3$ and MeCl over an Sn catalyzed Al fixed bed at 300° C. A 3:1 MeCl:Si feed ratio was used with a flow rate giving a residence time of about 5.0 seconds.

A carbon steel cylinder approximately 1.0 inch in diameter and 10 inches in height was filled with about 43.3 g of aluminum powder. The aluminum powder was Alcan 44, atomized aluminum powder, purchased from Alcan-Toyo American, Joliet, Ill. Mixed in with the aluminum powder was about 0.17 g of tin powder of less than about 325 mesh. The aluminum and tin powder mixture was held in place by a plug of glass wool. The cylinder was placed in an electrically heated fluidized sand bath to control the temperature of the cylinder and its contents. The reactor was heated to a temperature of about 300° C. under a nitrogen purge.

Methyl chloride (MeCl) was fed as a gas from a compressed gas cylinder. Methyl chloride flow was controlled by a mass flow meter at a rate of about 8.7 g/h. The organohalosilane feed, in this case methyltrichlorosilane (Me), began as a liquid feed from a positive displacement pump and was fed at a rate of about 8.7 to 8.9 g/h. The MeCl and organohalosilane feeds were passed through approximately 4 feet of coiled stainless steel tubing in the heated fluidized sand bath. Feed of reactants to the cylinder were from the top of the cylinder to the bottom. At the reactor temperature, the reactant gases were calculated to have a residence time of about 5 seconds. The feed resulted in a MeCl/Me mole ratio of about 3.0/1.

The vapors exiting the cylinder passed through a heated trap, temperature controlled at approximately 115° C., to remove $AlCl_3$ from the vapor stream as a solid. The remaining vapors were passed to a cold trap to recover the unreacted MeCl and the resultant methylchlorosilane mixture. The liquid crude produce was then analyzed by gas chromatography (GC). The results of this baseline run are summarized in Table 1. The term "Run#" serves as an identifier for a particular set of reaction conditions. The term "R-M" refers to the material used to retain the metal halide redistribution catalyst. "% R-M" refers to the weight percent of the retaining material present in relation to the aluminum metal. The percent conversion of the halosilane feed stream to multi-methylated silanes is denoted by "% Si Conv." The term "ADME" measures the additional Me-Si ligands formed per mole Si fed to the reaction. The terms "% Me4, % Me3, and % Me2" refer to $Me_4Si$, $Me_3SiCl$, and $Me_2SiCl_2$ respectively and are expressed as a weight percent of the total converted halosilane.

TABLE 1

Methylation of Methyltrichlorosilane by Methylchloride in the Presence of Aluminum: Baseline Results.

| Run # | R-M | % R-M | % Si Conv. | ADME | % Me4 | % Me3 | % Me2 |
|---|---|---|---|---|---|---|---|
| 175 | none | 0 | 4.8 | .154 | 94.3 | 2.2 | — |
| 176 | none | 0 | 5.0 | .161 | 93.4 | 2.0 | — |

The data presented in Table 1 indicate that in the absence of a redistribution catalyst the conversion of methyltrichlorosilane to multi-methylated silanes is low.

EXAMPLE 2

Various materials were tested for their ability to retain in situ formed metal halides in the reaction zone, as evidenced by increased methylation of methyltrichlorosilane, when compared to the baseline results of Example 1. With the exception of the addition of the retaining material to the process, all other materials and process parameters were similar to those of Example 1. A mixture of the retaining material with the aluminum and tin catalyst was prepared and placed in the reaction cylinder. The retaining materials tested were activated carbon, Calgon, Pittsburgh, PA; fumed silica, Cabot, Tuscon, AZ; and $Al_2O_3$, Harshaw, Elyria, OH. The concentrations tested are presented in Table 2 in the column labeled "% R-M." Concentrations are expressed as weight percent of the aluminum metal. The other headings are as described for Table 1.

TABLE 2

Effect of Retaining Material on Process For Methylation of Methyltrichlorosilane.

| Run # | R-M | % R-M | % Si Conv. | ADME | % Me4 | % Me3 | % Me2 |
|---|---|---|---|---|---|---|---|
| 177 | Carbon | 42 | 48.6 | .571 | 6 | 5 | 90 |
| 178 | Silica | 8 | 22.1 | .476 | 11 | 52 | 24 |
| 186 | $Al_2O_3$ | 42 | 9.5 | .276 | 23 | 40 | 24 |

In comparison to the baseline values of Table 1, the conversion of methyltrichlorosilane to higher methylated silanes was increased by the presence of a retaining material.

EXAMPLE 3

The effects of the reactor configuration was evaluated. Run number 178, as described in Example 2, where silica was mixed with the aluminum metal and tin catalyst, was compared to a process where the silica was separated from the aluminum metal and tin catalyst by a fiber glass plug. Silica at 8 weight percent of the aluminum was placed down stream from the aluminum metal and tin catalyst mixture. All other materials and process parameters where similar to those of Examples 1 and 2. Results are presented in Table 3. The headings of Table 3 are as described previously.

TABLE 3

Effect of Reactor Configuration on Retaining Material Ability to Retain a Redistribution Catalyst and Facilitate Methylation of Methyltrichlorosilane.

| Run # | R-M | Config. | % R-M | % Si Conv. | ADME | % Me4 | % Me3 |
|---|---|---|---|---|---|---|---|
| 178 | Silica | Mixed | 8 | 22.1 | .476 | 11 | 52 |
| 182 | Silica | Staged | 8 | 16.6 | .702 | 89 | 8 |

Both the staged and mixed configuration increased methylation of methyltrichlorosilane over that of the baseline values presented in Table 1.

EXAMPLE 4

The effect of temperature on the methylation of methyltrichlorosilane in the presence of silica was evaluated. The temperatures evaluated were 200° C., and 250° C. The fluidized sand bed containing the feed tube and reactor, as described in Example 1, was equilibrated at the desired experimental temperature prior to initiation of the test run. All materials and other process parameters were as presented in Examples 1 and 2. The results of this evaluation are presented in Table 4 along with the results of run number 178 of Example 2, which was ran at 300° C. Table headings are as previously described.

TABLE 4

Effect of Temperature on The Methylation of Methyltrichlorosilane in The Presence of Silica.

| Run # | Temp. | R-M | % R-M | % Si Conv. | ADME | % Me4 | % Me3 | % Me2 |
|---|---|---|---|---|---|---|---|---|
| 190 | 200° C. | Silica | 8 | 0 | 0 | — | — | — |
| 181 | 250° C. | Silica | 8 | 19 | .595 | 69 | 4 | 19 |
| 178 | 300° C. | Silica | 8 | 22 | .476 | 11 | 52 | 24 |

This study indicates that this process has a lower temperature limit of 200° C., at which temperature no methylation occurred. The process, as described, is effective at temperatures of 250° C. and 300° C., with the 250° C. temperature providing slightly better ADME values.

What is claimed is:

1. A process for preparing multi-organic substituted silanes having the formula,

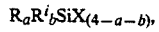

$$R_aR^i{}_bSiX_{(4-a-b)},$$

where each R is independently selected from the group consisting of methyl, ethyl, and n-propyl; each $R^i$ is independently selected from a group consisting of alkyl, substituted alkyl, alkenyl, aryl, and alkaryl groups; a has a value of 1, 2, 3, or 4, b has a value of 0, 1, 2, or 3 and the sum of a+b is 2, 3, or 4; and X is a halogen atom, the process comprising (A) contacting a halide of silicon, having the formula,

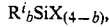

$$R^i{}_bSiX_{(4-b)},$$

where $R^i$, b, and X are defined above; with an alkyl halide, having the formula,

$$RX;$$

where R and X are defined above, in the presence of a metal which serves as a halogen acceptor;
(B) reacting the halide of silicon with the alkyl halide in the presence of the metal at a temperature greater than 200° C. to form an initial reaction mixture; and
(C) contacting the initial reaction mixture with a redistribution catalyst;
(D) isolating and separating the multi-organic substituted silane.

2. A process according to claim 1, where the redistribution catalyst consists essentially of a metal halide retained by a solid support material.

3. A process according to claim 2, where the temperature is between 200° C. and 450° C.

4. A process according to claim 3, where the metal is selected from the group consisting of aluminum and zinc.

5. A process according to claim 4, where the metal is aluminum.

6. A process according to claim 4, where the metal halide is part of the initial reaction mixture and is retained in situ by the solid support material.

7. A process according to claim 6, where the solid support material is selected from the group consisting of silica, carbon, silica gel, and $Al_2O_3$.

8. A process according to claim 7, where the solid support material is selected from the group consisting of silica, carbon, and $A_2O_3$.

9. A process according to claim 7, where the solid support material is separate from the metal.

10. A process according to claim 7, where each R and $R^i$ are independently selected from the group consisting of methyl and ethyl.

11. A process according to claim 10, where R is methyl, the metal is aluminum, and the solid support material is about 8 to 20 weight percent of the metal.

12. A process according to claim 4, further comprising a sufficient quantity of a catalyst effective in improving exchange of X atoms of the alkyl halide and halide of silicon with the metal which serves as a halogen acceptor.

13. A process according to claim 12, where the catalyst is selected from the group consisting of tin and tin compounds, antimony and antimony compounds, copper and copper compounds, aluminum bromide, boron, phosphorous and phosphorous compounds, palladium, iodine, iron halides, hydrogen halides, mercury and mercury compounds, and mixtures thereof.

14. A process according to claim 12, where the metal is aluminum and the catalyst is selected from the group consisting of zinc and zinc compounds, tin and tin compounds, antimony and antimony compounds, copper and copper compounds, aluminum bromide, boron, phosphorous and phosphorous compounds, palladium, iodine, iron halides, hydrogen halides, mercury and mercury compounds, and mixtures thereof.

15. A process according to claim 12, where the catalyst is present as a discrete mixture with the metal.

16. A process according to claim 12, where the catalyst is present as an alloy with the metal.

17. A process according to claim 15, where the catalyst is selected from the group consisting of tin metal and tin compounds.

18. A process according to claim 17, where R and $R^i$ are independently selected from the group consisting essentially of methyl and ethyl.

19. A process according to claim 18, where the halogen-accepting metal is aluminum.

20. A process according to claim 19, where R is methyl and silica is present at about 8 weight percent of the metal.

21. A process according to claim 1, where isolating and separating the multi-organic substituted silanes comprises
(E) first separating the non-retained metal halide from gaseous multi-organic substituted silanes, unreacted halide of silicon, and unreacted alkyl halide; and
(F) then isolating the multi-organic substituted silanes from the unreacted halide of silicon and the alkyl halide.

22. A process for preparing mono-alkylated silanes having the formula, $RSiX_3$, where R is selected from the group consisting of methyl, ethyl, and n-propyl; and X is a halogen atom, the process comprising
(A) contacting a halide of silicon, having the formula, $SiX_4$, where X is defined above; with an alkyl halide having the formula,

RX, where R and X are defined above, in the presence of a metal which serves as a halogen acceptor;
(B) reacting the halide of silicon with the alkyl halide in the presence of the metal at a temperature greater than 200° C. to form an initial reaction mixture; and
(C) contacting the intial reaction mixture with a redistribution catalyst;
(D) isolating and separating the mono-alkylated silane.

23. A process according to claim 22, where the metal is selected from the group consisting of aluminum and zinc.

24. A process according to claim 22, where R is selected from the group consisting of methyl and ethyl.

25. A process according to claim 24, where the redistribution catalyst is aluminum chloride retained on a solid support material.

26. A process according to claim 22, further comprising a sufficient quantity of a catalyst effective in improving exchange of X atoms of the alkyl halide and halide of silicon with the metal which serves as a halogen acceptor.

27. A process according to claim 26, where the catalyst is selected from the group consisting of tin and tin compounds, antimony and antimony compounds, copper and copper compounds, aluminum bromide, boron, phosphorous and phosphorous compounds, palladium, iodine, iron halides, hydrogen halides, mercury and mercury compounds, and mixture thereof.

28. A process according to claim 26, where metal is aluminum and the catalyst is selected from the group consisting of zinc and zinc compounds, tin and tin compounds, antimony and antimony compounds, copper and copper compounds, aluminum bromide, boron, phosphorous and phosphorous compounds, palladium, iodine, iron halides, hydrogen halides, mercury and mercury compounds, and mixtures thereof.

* * * * *